(12) United States Patent
Johnson et al.

(10) Patent No.: US 6,509,960 B2
(45) Date of Patent: Jan. 21, 2003

(54) METHOD AND APPARATUS EMPLOYING EXTERNAL LIGHT SOURCE FOR ENDPOINT DETECTION

(75) Inventors: David R. Johnson, Meridian, ID (US); Joe Lee Phillip, Nampa, ID (US); Todd C. Nielsen, Meridian, ID (US); Robert J. Hatfield, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 4 days.

(21) Appl. No.: 09/796,232

(22) Filed: Feb. 28, 2001

(65) Prior Publication Data

US 2001/0009459 A1 Jul. 26, 2001

Related U.S. Application Data

(63) Continuation of application No. 09/399,242, filed on Sep. 20, 1999, now Pat. No. 6,429,928, which is a continuation of application No. 08/963,508, filed on Nov. 4, 1997, now Pat. No. 5,969,805.

(51) Int. Cl.⁷ .......................... G01B 11/00; G01N 21/64
(52) U.S. Cl. ...................... 356/72; 250/458.1; 356/417; 216/60
(58) Field of Search .................. 356/73, 72; 250/459.1, 250/461.1, 461.2, 458.1; 216/60

(56) References Cited

U.S. PATENT DOCUMENTS

| | | | |
|---|---|---|---|
| 4,198,261 A | 4/1980 | Busta et al. | |
| 4,377,436 A | 3/1983 | Donnelly et al. | |
| 4,462,863 A | 7/1984 | Nishimatsu et al. | |
| 4,482,424 A | 11/1984 | Katzir et al. | |
| 4,500,918 A | * 2/1985 | Koumura et al. | ........... 358/514 |
| 4,800,282 A | 1/1986 | Nishimura | |
| 4,586,822 A | 5/1986 | Tanimoto | |
| 4,609,428 A | 9/1986 | Fujimura | |
| 4,846,920 A | 7/1989 | Keller et al. | |
| 5,162,867 A | 11/1992 | Kohno | |
| 5,176,790 A | 1/1993 | Arleo et al. | |
| 5,257,047 A | 10/1993 | Haneda et al. | |
| 5,264,328 A | 11/1993 | DellaGuardia et al. | |
| 5,308,447 A | * 5/1994 | Lewis et al. | ................... 216/23 |
| 5,312,717 A | 5/1994 | Sachdev et al. | |
| 5,350,236 A | 9/1994 | Thakur et al. | |
| 5,362,356 A | 11/1994 | Schoenborn | |
| 5,397,431 A | 3/1995 | Kadomura | |
| 5,434,026 A | 7/1995 | Takatsu et al. | |
| 5,444,265 A | 8/1995 | Hamilton | |
| 5,447,598 A | 9/1995 | Mihara et al. | |
| 5,483,568 A | 1/1996 | Yano et al. | |
| 5,489,362 A | 2/1996 | Steinhardt et al. | |
| 5,552,016 A | 9/1996 | Ghanayem | |
| 5,567,268 A | 10/1996 | Kadomura | |
| 5,654,237 A | 8/1997 | Suguro et al. | |
| 5,672,091 A | 9/1997 | Takahashi et al. | |
| 5,900,103 A | * 5/1999 | Tomoyasu et al. | ....... 118/723 E |
| 5,969,805 A | 10/1999 | Johnson et al. | |

FOREIGN PATENT DOCUMENTS

| | | | |
|---|---|---|---|
| JP | 3-165518 A | * | 7/1991 |
| JP | 3-194917 | | 8/1991 |
| JP | 4-164316 | | 6/1992 |
| JP | 4-280650 | | 10/1992 |
| JP | 8-220010 A | * | 8/1996 |

OTHER PUBLICATIONS

IBM Technical Disclosure Bulletin, vol. 29, No. 6, Nov. 1986, pp. 2796–2797.*

* cited by examiner

Primary Examiner—F. L. Evans
(74) Attorney, Agent, or Firm—TraskBritt

(57) ABSTRACT

A method and apparatus for endpoint detection for the stripping of a particular material, such as photo-resist material, from a substrate surface. A beam of light is projected onto the substrate surface and the fluoresced and/or reflected light intensity at a particular wavelength band is measured by a light detector. The light intensity is converted to a numerical value and transmitted electronically to a control mechanism which determines the proper disposition of the substrate. The control mechanism controls the cessation of the stripping process and may control a substrate-handling device which sequentially transfers substrates to and from a stripping chamber.

42 Claims, 2 Drawing Sheets

METHOD AND APPARATUS EMPLOYING EXTERNAL LIGHT SOURCE FOR ENDPOINT DETECTION

CROSS-REFERENCE TO RELATED APPLICATION

This application is a continuation of application Ser. No. 09/399,242, filed Sep. 20, 1999, now U.S. Pat. No. 6,429,928 B2, issued Aug. 6, 2002, which is a continuation of application Ser. No. 08/963,508, filed Nov. 4, 1997, now U.S. Pat. No. 5,969,805, issued Oct. 19, 1999.

BACKGROUND OF THE INVENTION

1. Field of the Invention

This invention relates generally to the manufacture of semiconductor devices prepared by a method including photolithography. More particularly, this invention pertains to a method for inspecting semiconductor substrates to determine the completion of stripping ("endpoint") during a plasma stripping process to remove a photo-resist material from a semiconductor substrate surface after photolithography.

2. State of the Art

Semiconductor chips are produced in a multi-step process by which a plurality of identical electronic circuits is typically formed on a semiconductor substrate, such as a silicon wafer. The semiconductor substrate is then subdivided (diced) into individual chips which are further processed into packaged semiconductor devices or otherwise secured in higher-level packaging for ultimate use.

The electronic circuits are generally patterned into a semiconductor substrate by a series of steps including photolithography. To elaborate, a photo-resist material is coated onto the semiconductor substrate surface. As disclosed in commonly owned U.S. Pat. No. 5,350,236 issued Sep. 27, 1994, hereby incorporated herein by reference, the temperature of a semiconductor substrate during the application of a material can be monitored by measuring light reflected from a surface of the semiconductor substrate, such that the material and semiconductor substrate are not overheated.

After the photo-resist material has been coated on the semiconductor substrate surface, it is selectively exposed to a radiation source, such as by the passage of radiation (i.e., light, e-beam, or X-rays) through a mask having a desired aperture pattern defined therein. If a positive photo-resist material is used, the exposure to the radiation source converts the positive photo-resist material to a more soluble state which allows the exposed positive photo-resist to be removed with a solvent, thereby leaving a pattern substantially identical to the mask. If a negative photo-resist material is used, the exposure to the radiation source converts the negative photo-resist material to a less soluble state which allows the unexposed positive photo-resist to be removed with a solvent, thereby leaving a pattern substantially identical to the openings in the mask. Whether a positive or a negative photo-resist material is used, the photolithographic process results in a photo-resist pattern which will become the electronic circuit pattern on a semiconductor substrate.

Following the removal of the portions of the photo-resist material in the development process, the semiconductor substrate is subjected to further processing steps which may include doping, etching, and/or deposition of conductive materials in unprotected areas, i.e., areas devoid of photo-resist material. After one or more of these processing steps, the semiconductor substrate is subjected to a stripping step to remove the photo-resist material remaining on the semiconductor substrate.

The stripping of photo-resist material is commonly achieved using plasma etching. In plasma etching, a glow discharge is used to produce at least one reactive species, such as atoms, radicals, and/or ions, from relatively inert gas molecules. Basically, a plasma etching process comprises 1) at least one reactive species is generated in a plasma from a bulk gas, 2) the reactive species diffuses to a surface of a material being etched, 3) the reactive species is absorbed on the surface of the material being etched, 4) a chemical reaction occurs which results in the formation of at least one volatile by-product, 5) the by-product is desorbed from the surface of the material being etched, and 6) the desorbed by-product diffuses into the bulk gas. The materials used as photo-resist are generally organic polymers, such as phenol-formaldehyde, polyisoprene, poly-methyl methacrylate, poly-methyl isopropenyl ketone, poly-butene-1-sulfone, poly-trifluoroethyl chloroacrylate, and the like. Such photo-resist materials are generally etched in plasmas containing pure oxygen to produce species that attack the organic materials to form $CO$, $CO_2$, and $H_2O$ as volatile by-products.

After the removal of the photo-resist material, a subsequent processing step may include heating the semiconductor substrate in a diffusion furnace or applying a layer of material with a chemical vapor deposition system. Occasionally, a semiconductor substrate is inadvertently passed to a thermal furnace or vapor deposition system with incomplete removal of the photo-resist material. The resulting damage to the processing equipment may be severe. For example, furnace diffusion tubes are irreparably damaged by vaporized hydrocarbons and carbon from the photo-resist material and, thus, the furnace diffusion tubes must be replaced. The replacement equipment and/or the downtime to repair the processing equipment is usually very costly.

Furthermore, the photo-resist carrying semiconductor substrate and one or more subsequent semiconductor substrates entering the processing equipment prior to shutdown of the equipment are usually also contaminated and must be discarded. At a late stage of manufacture, a semiconductor substrate may have a value between about $10,000 and $20,000. Thus, even an occasional loss is significant.

Therefore, it is very important that completion ("endpoint") of the photo-resist stripping be accurately detected. A common endpoint detection method with plasma etching is disclosed in U.S. Pat. No. 4,377,436 issued Mar. 22, 1983 to Donnelly et al. wherein endpoint detection during plasma-assisted etching is signaled by cessation or onset of spatially confined luminescence resulting from an etch reaction product. The light source for the luminescence comes from the plasma generation. However, as the use of microwave plasma etching has developed, the generation of the plasma has been removed from the etching chamber. The removal of the plasma generation from the etching chamber prevents excess heat buildup in the etching chamber caused by the plasma generation and allows for different frequencies and wavelengths to be used to create free radicals (i.e., the reactive species).

The reactive species is formed remotely in a microwave reaction chamber and transported to the etching chamber, such as shown in U.S. Pat. No. 5,489,362 issued Feb. 6, 1996 to Steinhardt et al. No plasma is present in the stripping chamber with such a microwave plasma system. Therefore, there is no light source present in the chamber that can be used for detection of the endpoint removal of the photo-resist material.

Therefore, it would be advantageous to develop an apparatus and method of luminescent endpoint detection for the stripping of materials in a microwave plasma etching system employing a plasma chamber separate from its etching chamber.

SUMMARY OF THE INVENTION

The present invention is an automated method and apparatus for determining the endpoint of the removal of a photo-resist material on the surface of a semiconductor substrate by the detection of fluorescence, reflection, or absorption of light by the photo-resist material. Hereinafter, the term "emanated light" is defined as the light resulting from a light striking the photo-resist material or other material including fluoresced light, reflected light, or absorbed light.

As mentioned above, photo-resist materials are generally organic polymers, such as phenol-formaldehyde, polyisoprene, poly-methyl methacrylate, poly-methyl isopropenyl ketone, poly-butene-1-sulfone, poly-trifluoroethyl chloroacrylate, and the like. Organic substances can generally fluoresce (luminescence that is caused by the absorption of radiation at one wavelength followed by nearly immediate re-radiation at a different wavelength) or will absorb or reflect light. Fluorescence of the photo-resist material at a particular wavelength, or reflection/absorption by the photo-resist material of light at a given wavelength, may be detected and measured, provided the material differs from the underlying semiconductor substrate in fluorescence or reflection/absorption at a selected wavelength or wavelengths. For example, a positive photo-resist generally fluoresces red or red-orange and a negative photo-resist generally fluoresces yellow.

In a particular application of the invention, the presence of photo-resist material on a semiconductor substrate surface may be rapidly and automatically determined, recorded, and used to determine when the photo-resist material has been removed from the semiconductor substrate surface. In a preferred application of the present invention, a semiconductor substrate is introduced into a stripping chamber which receives at least one reactive species, usually generated from oxygen, from a microwave plasma generator. The stripping chamber includes a first optical port and a second optical port positioned in a wall of the stripping chamber. A beam of light from a lamp passes through the first port, strikes the photo-resist material on the semiconductor substrate and is reflected as an emanated beam at an angle through the second optical port. Preferably, the photo-resist material differs from the semiconductor substrate in fluorescence, absorption, and/or reflection properties at some wavelengths of incident light.

The intensity of the emanated light will decrease when the photo-resist is stripped away. When the intensity has decreased to a level indicating that the photo-resist has been completely stripped away, the stripping process can be terminated. This detection method also allows the system to generate an error signal if the level indicating that the photo-resist has been stripped is not reached within a certain amount of time. Such an error signal would indicate that a semiconductor substrate was stripping poorly (i.e., too slowly) or the stripping equipment was not functioning properly. This error signal allows for the culling of the offending semiconductor substrate for rework or allows for the stripping equipment to be shut down for repair, which prevents the spread of photo-resist material contamination throughout other process steps. Furthermore, the throughput of the stripping equipment can be increased because empirically established finite strip times used in conjunction with endpoint detection of the photo-resist removal prevents the need for exaggerated strip times to ensure complete stripping.

In this invention, the semiconductor substrate is irradiated with light, which light may be monochromatic, multichromatic, or white. In one variation, the intensity of generated fluorescence particular to the photo-resist material at a given wavelength is measured. In another variation, the intensity is measured at a wavelength which is largely or essentially fully absorbed by the photo-resist material. In a further variation, the intensity of reflected light is measured at a particular wavelength highly reflected by the photo-resist material but absorbed by the substrate.

The intensity of the emanated light is measured by a sensing apparatus and the result inputted to a logic circuit, e.g., a programmable computer. The result may be recorded and used for a decision making step or to activate a culling device.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

Figure 1:
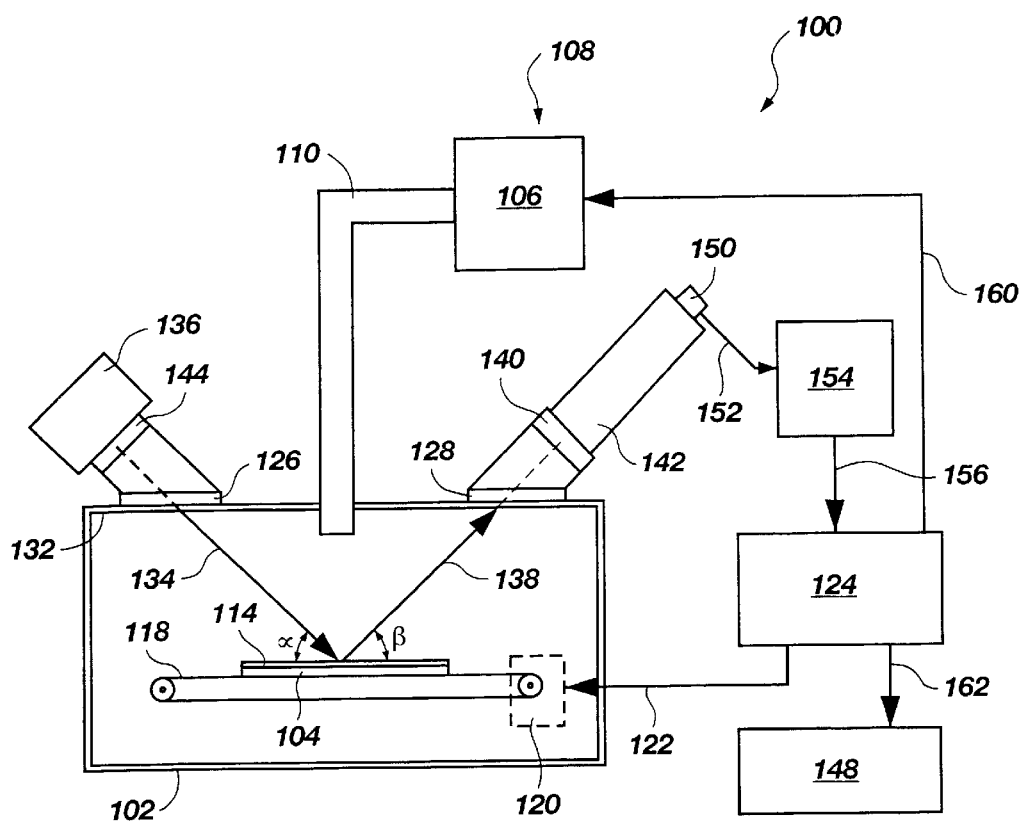
FIG. 1 is a diagrammatic view of a photo-resist material stripping apparatus of the present invention.

FIG. 1 illustrates a stripping apparatus 100 of the present invention. It should be understood that the apparatus 100 of FIG. 1 is not meant to be an actual view of any particular stripping device, but is merely an idealized representation which is employed to more clearly and fully depict the process of the invention than would otherwise be possible.

The stripping apparatus 100 comprises a stripping chamber 102 having one or more entryways or portals (not shown) for the introduction and removal of semiconductor substrates, such as semiconductor substrate 104, into and from the stripping chamber 102. The semiconductor substrate 104 may be a semiconductor material comprising a slice of crystalline silicon (silicon wafer) or may include various semiconductive material or material layers, including without limitation, silicon wafers, silicon-on-insulative (SOI) structure, silicon-on-sapphire (SOS) structure, gallium arsenide, or germanium.

The stripping apparatus 100 also includes a microwave plasma generator 106 which generates reactive species in a plasma from an oxygen containing gas 108 fed to the plasma generator 106. The reactive species travel down waveguide 110 into the stripping chamber 102.

A photo-resist material detection apparatus is integrated with the stripping chamber 102 for in situ automated determination of the progress in stripping of a photo-resist material 114 from the semiconductor substrate 104. Preferably, the photo-resist material 114 differs from the semiconductor substrate 104 in fluorescing, absorption, and/or reflection properties at some wavelengths of incident light. The semiconductor substrate 104 is shown on a movable stage 118 within the stripping chamber 102 to provide the desired positioning of the semiconductor substrate 104 with respect to a primary high energy beam 134. The movable stage 118 may be movable by one or more stepper motors 120 (shown in shadow lines) or other motive means controlled by electronic signals 122 from a control mechanism 124, such as a programmed general purpose computer, i.e., a personal computer driving appropriate switches.

The photo-resist material detection apparatus includes two optical ports, a first optical port 126 and a second optical port 128, which are positioned in an upper wall 132 of the stripping chamber 102. The primary high energy beam 134 of light from a high energy lamp 136 passes through the first optical port 126, strikes the photo-resist material 114 of the semiconductor substrate 104 at an angle of incidence α and is reflected as an emanated beam 138 at an angle of departure β (substantially equal to angle of incidence α) through the second optical port 128. Although the beam 134 may irradiate the entire surface of the semiconductor substrate 104 simultaneously, the beam 134 is preferably a sheet beam having a width (perpendicular to the plane of the drawing sheet) approximately the width of the semiconductor substrate 104. The semiconductor substrate 104 can be passed under the sheet beam using movable stage 118, enabling the inspection of the entire surface of the semiconductor substrate 104.

Figure 2:
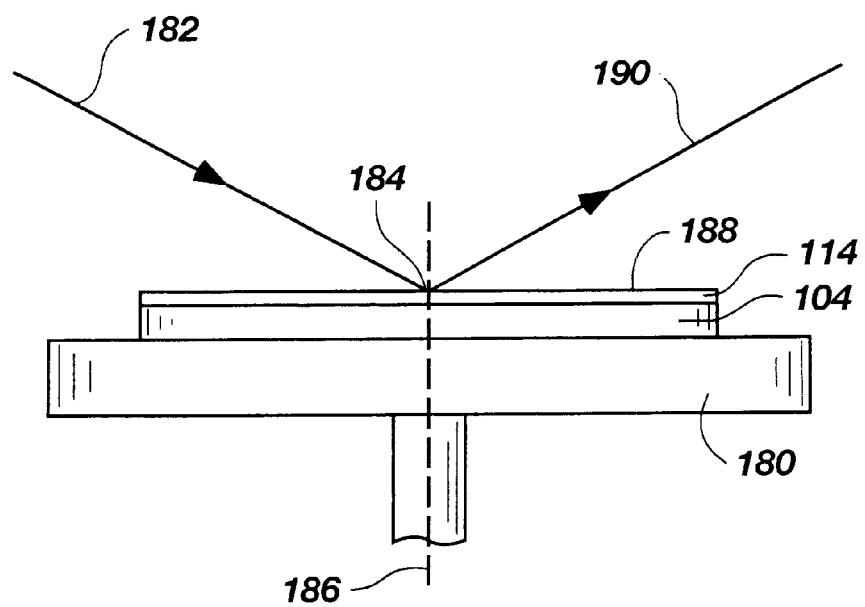
FIG. 2 is a side view of an alternate photo-resist material stripping apparatus of the present invention.

Furthermore, as illustrated in FIG. 2, the semiconductor substrate 104 can be positioned on a rotating platform 180, wherein a sheet beam 182 is directed to a center point 184 of the photo-resist material 114 on the semiconductor substrate 104 and extends across the width (perpendicular to the plane of the drawing sheet) of the semiconductor substrate 104 resulting in emanated beam 190. The rotatable platform 180 is rotated about axis 186 such that the entire surface 188 of the photo-resist material 114 is contacted by the sheet beam 182. This allows for different perspectives of the photo-resist material surface 188 which will detect photo-resist material 114 that may be in a "shadow" due to the topography of the semiconductor substrate 104, if only one particular perspective is taken.

Returning to FIG. 1, fluoresced and/or reflected light produced by existing photo-resist material 114 in response to the beam 134 is also present in the emanated beam 138. The emanated beam 138 may be passed through an optical band pass filter or suppression filter 140 to absorb non-fluoresced light or undesired reflected light and produce a filtered light beam substantially free of such undesired wavelengths. For example, the emanated beam 138 may be passed through the optical band pass filter 140 to produce a light beam having a narrow wavelength band of, for example, 700 nm+/−80 nm. Such a wavelength is a characteristic fluorescing emission of commonly used positive photo-resist materials, as listed above.

The emanated beam 138 is transmitted into a photo-multiplier tube 142 for the ultimate generation of an electronic signal 156 indicative of the light intensity at the filtered light wavelength. The electronic signal 156 may be generated by a light intensity sensor 150, such as a silicon diode sensor, which generates an analog intensity signal 152. The intensity signal 152 is sent to a power meter 154 including an analog-to-digital converter, which converts the intensity signal 152 into an electronic binary numerical value comprising the electronic signal 156. The electronic signal 156 is preferably processed by a software program in the control mechanism 124 (preferably a programmed computer). It is, of course, understood that analog to digital conversion is not a necessary limitation. The control mechanism 124 can be configured to receive an analog signal directly.

The control mechanism 124 determines whether stripping endpoint has occurred and sends a cessation signal 160 to the microwave plasma generator 106 if endpoint is detected or if the endpoint is not detected within a predetermined time frame. The control mechanism 124 also provides transfer instructions 162 to a wafer transfer device 148 based on electronic signal 156. The transfer instructions 162 are generated for either the detection of stripping endpoint or for the rejection of the semiconductor substrate 104. The transfer instructions 162 will trigger the placement and retrieval of the semiconductor substrate 104 into the stripping chamber 102 and from the stripping chamber 102 after the test to another location for further processing. The electronic signals 122 for stage control are also sent by the control mechanism 124 for controlling motion of the movable stage 118.

Figure 3:
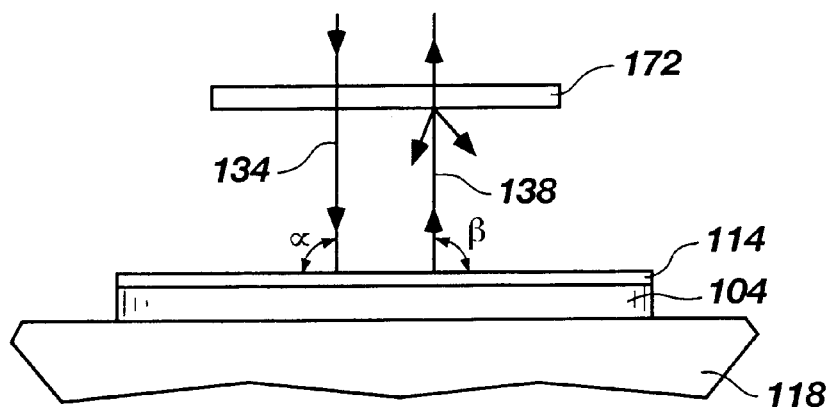
FIG. 3 is a side view of an alternate light detection configuration of the present invention.

As illustrated in FIG. 1, the beam 134 is shown striking the photo-resist material 114 on the semiconductor substrate 104 at the angle of incidence α of about 45 degrees and the emanated beam 138 is shown reflected at the angle of departure β of about 45 degrees. The incident angle α for the beam 134 and the departure angle β for the emanated beam 138 are preferably between 0 and 45 degrees. However, by using a dichromatic mirror 172 (a mirror which reflects wavelengths of less than a given value, and passes wavelengths greater than the given value) as shown in FIG. 3, the beam 134 and the emanated beam 138 may both pass through the same port, and incident angle α and the departure angle β are both 90 degrees (i.e., perpendicular to the semiconductor substrate 104). The emanated beam 138 is shown offset from the beam 134 for the sake of clarity.

The high energy lamp 136 is preferably a mercury or xenon lamp which produces high intensity, fluorescence-inducing illumination. The light output from the high energy lamp 136 may be filtered by a band pass or excitation filter 144 for removing wavelengths from the primary high energy beam 134 which do not stimulate fluorescence, reflect, or absorb in the semiconductor substrate 104.

As indicated, the method depends upon a difference in fluorescence or light absorption/reflectance between the material to be detected, e.g., the photo-resist and the underlying substrate. A wavelength of incident illumination is typically chosen which maximizes the difference in fluorescence, absorption, or reflectance. It is preferred to use fluorescence as the measured output, but light absorbance may be used when the material to be detected strongly absorbs a particular wavelength of radiation while the substrate strongly reflects the same.

It should be understood that references herein to light of a particular "wavelength" encompass wavelength bands that are "about" a particular wavelength. In other words, the term "a particular wavelength" may include wavelengths both slightly longer and shorter than the "particular wavelength".

Having thus described in detail preferred embodiments of the present invention, it is to be understood that the invention defined by the appended claims is not to be limited by particular details set forth in the above description, as many apparent variations thereof are possible without departing from the spirit or scope thereof.

What is claimed is:

1. A method for stripping endpoint detection of a photo-resist material on a substrate surface, comprising:
   positioning a substrate having photo-resist material on a substrate surface thereof on a movable stage;
   illuminating a portion of the substrate surface with a stationary sheet beam of light from a selected first direction with respect to the substrate surface, the stationary sheet beam of light having a width at least approximately equal to a width of the substrate;
   collecting from a fixed location, emanated light from the illumination of the portion of the substrate surface;
   moving the movable stage relative to the stationary sheet beam of light to illuminate the entire substrate surface and collect emanated light from the entire substrate surface;
   generating a signal indicative of an intensity of the emanated light; and
   providing at least one of a plasma generation cessation signal, a substrate transfer signal and a movable stage control signal, responsive at least in part to the signal indicative of the intensity of the emanated light.

2. The method of claim 1, wherein the positioning of the substrate is conducted within an etching chamber and further comprising etching at least a portion of the photo-resist material on the substrate surface.

3. The method of claim 2, wherein moving the movable stage relative to the stationary sheet beam of light comprises rotating the movable stage about an axis such that the entire substrate surface is contacted by the stationary sheet beam of light.

4. The method of claim 2, wherein providing a plasma generation cessation signal comprises generating an instruction for transmission to a plasma generator.

5. The method of claim 4, wherein generating an instruction for transmission to a plasma generator comprises generating the instruction upon detecting an endpoint for said etching at least a portion of the photo-resist material on the substrate surface.

6. The method of claim 4, wherein said generating an instruction for transmission to a plasma generator comprises generating the instruction if an endpoint for said etching at least a portion of the photo-resist material is not detected within a predetermined time frame.

7. The method of claim 2, wherein said providing a substrate transfer signal comprises generating an instruction for transmission to an automated substrate handling apparatus to control disposition of the substrate.

8. The method of claim 7, wherein generating an instruction for transmission to said automated substrate handling apparatus comprises instructing the automated substrate handling apparatus to retrieve the substrate from the etching chamber for further processing upon detecting an endpoint for said etching at least a portion of the photo-resist material on the substrate surface.

9. The method of claim 7, wherein said generating an instruction for transmission to said automated substrate handling apparatus comprises instructing the automated substrate handling apparatus to retrieve the substrate from the etching chamber for rejection if an endpoint for said etching at least a portion of the photo-resist material is not detected within a predetermined time frame.

10. The method of claim 1, wherein said generating a signal indicative of an intensity of the emanated light comprises detecting the presence of a selected wavelength of fluoresced light characteristic of the photo-resist material.

11. The method of claim 10, further comprising filtering the stationary sheet beam of light while illuminating a portion of the substrate surface to remove non-fluorescence producing light wavelengths from the stationary sheet beam of light.

12. The method of claim 1, wherein said generating a signal indicative of an intensity of the emanated light comprises detecting the absence of a selected wavelength of light characteristically substantially absorbed by the photo-resist material and substantially reflected by the substrate.

13. The method of claim 12, further comprising filtering the stationary sheet beam of light while illuminating a portion of the substrate surface to limit light transmission to wavelengths substantially absorbed by the photo-resist material and substantially reflected by the substrate.

14. The method of claim 1, wherein said generating a signal indicative of an intensity of the emanated light comprises detecting the presence of a selected wavelength of light characteristically substantially reflected by the photo-resist material and substantially absorbed by the substrate.

15. The method of claim 14, further comprising filtering the stationary sheet beam of light while illuminating a portion of the substrate surface to limit light transmission to wavelengths substantially reflected by the photo-resist material and substantially absorbed by the substrate.

16. The method of claim 1, wherein said generating a signal indicative of an intensity of the emanated light comprises passing the emanated light through a photo-multiplier tube to generate the signal.

17. The method of claim 1, wherein said illuminating a portion of the substrate surface with a stationary sheet beam of light from the selected first direction with respect to the substrate surface comprises passing the stationary sheet beam of light through a first side of a dichromatic mirror at an angle substantially perpendicular to the substrate surface.

18. The method of claim 17, wherein collecting emanated light from the illumination of the portion of the substrate surface comprises passing a portion of the emanated light having wavelengths greater than a given value through a second side of the dichromatic mirror at an angle substantially perpendicular to the substrate surface, and reflecting a portion of the emanated light having wavelengths less than a given value off of the second side of the dichromatic mirror.

19. An apparatus for determining an endpoint for stripping of a material from a substrate surface, comprising:
   a stripping chamber having a plasma generator and a movable stage for receiving a substrate thereon;
   at least one high energy light source;
   a first optical apparatus configured to form a stationary sheet beam of light directed to a preselected location at a first angle relative to the movable stage;
   a second optical apparatus configured to collect and filter emanated light from the preselected location at a second angle relative to the movable stage;
   a light intensity sensing apparatus configured to receive the filtered emanated light, measure an intensity thereof, and generate a signal representative of the measured light intensity; and
   a control mechanism configured to process the signal representative of the measured light intensity and to control the plasma generator and the movable stage.

20. The apparatus of claim 19, further comprising an automated substrate handling apparatus for moving a substrate into and out of the stripping chamber.

21. The apparatus of claim 20, wherein the control mechanism is further configured to control the automated substrate handling apparatus.

22. The apparatus of claim 20, further comprising a plurality of sites for selective movement of the substrate thereto from the stripping chamber by the automated substrate handling apparatus.

23. The apparatus of claim 19, wherein the movable stage is configured to rotate about a central axis.

24. The apparatus of claim 19, wherein the movable stage is configured to pass under the stationary sheet beam of light.

25. The apparatus of claim 19, wherein the first optical apparatus further comprises a primary band pass filter for restricting the high energy light source to a predetermined wavelength of light.

26. The apparatus of claim 25, wherein the primary band pass filter is configured to selectively pass fluorescence producing wavelengths of light for a material.

27. The apparatus of claim 25, wherein the primary band pass filter is configured to selectively pass light wavelengths which are substantially absorbed by the material and substantially reflected by the substrate.

28. The apparatus of claim 25, wherein the primary band pass filter is configured to selectively pass light wavelengths which are substantially reflected by the material and substantially absorbed by the substrate.

29. The apparatus of claim 19, wherein the at least one high energy light source comprises a xenon lamp.

30. The apparatus of claim 19, wherein the light intensity sensing apparatus comprises a silicon diode sensor.

31. The apparatus of claim 30, further comprising a power meter for converting the signal representative of the measured light intensity into a digital form.

32. The apparatus of claim 19, wherein the light intensity sensing apparatus comprises a photo-multiplier tube having a signal output.

33. An apparatus for determining an endpoint for stripping of a material from a substrate surface, comprising:

a stripping chamber having a plasma generator and a movable stage for receiving a substrate thereon;

a dichromatic mirror positioned above the movable stage;

at least one high energy light source positioned above the dichromatic mirror and configured to form a stationary sheet beam of light directed through the dichromatic mirror at an angle substantially perpendicular to the movable stage;

a light intensity sensing apparatus positioned above the dichromatic mirror and configured to receive light emanated through the dichromatic mirror at an angle substantially perpendicular to the movable stage, measure an intensity thereof, and generate a signal representative of the measured light intensity; and a control mechanism configured to process the signal representative of the measured light intensity and to control the plasma generator and the movable stage.

34. The apparatus of claim 33, further comprising an automated substrate handling apparatus for moving a substrate into and out of the stripping chamber.

35. The apparatus of claim 34, wherein the control mechanism is further configured to control the automated substrate handling apparatus.

36. The apparatus of claim 34, further comprising a plurality of sites for selective movement of a substrate thereto from the stripping chamber by the automated substrate handling apparatus.

37. The apparatus of claim 33, wherein the movable stage is configured to rotate about a central axis.

38. The apparatus of claim 33, wherein the movable stage is configured to pass under the stationary sheet beam of light.

39. The apparatus of claim 33, wherein the at least one high energy light source comprises a xenon lamp.

40. The apparatus of claim 33, wherein the light intensity sensing apparatus comprises a silicon diode sensor.

41. The apparatus of claim 40, further comprising a power meter for converting the signal representative of the measured light intensity into a digital form.

42. The apparatus of claim 33, wherein the light intensity sensing apparatus comprises a photo-multiplier tube having a signal output.

* * * * *